United States Patent
Bieber et al.

(10) Patent No.: US 7,610,490 B2
(45) Date of Patent: Oct. 27, 2009

(54) METHOD AND ARRANGEMENT FOR CONTROLLING ACCESS TO SENSITIVE DATA STORED IN AN APPARATUS, BY ANOTHER APPARATUS

(75) Inventors: Bernt Bieber, Hausen (DE); Dirk Weseloh, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 813 days.

(21) Appl. No.: 11/026,494

(22) Filed: Dec. 30, 2004

(65) Prior Publication Data

US 2005/0174988 A1    Aug. 11, 2005

(30) Foreign Application Priority Data

Dec. 30, 2003    (DE) ................. 103 61 800

(51) Int. Cl.
*G06F 21/00* (2006.01)
*G06F 7/04* (2006.01)
*G06F 7/00* (2006.01)
*G06F 19/00* (2006.01)

(52) U.S. Cl. .............. 713/183; 726/27; 707/9; 705/3

(58) Field of Classification Search ........ 705/3; 707/9; 713/183; 726/27

See application file for complete search history.

(56) References Cited

U.S. PATENT DOCUMENTS

| | | | | |
|---|---|---|---|---|
| 5,526,428 A * | 6/1996 | Arnold | ............ | 713/159 |
| 5,867,821 A * | 2/1999 | Ballantyne et al. | ............ | 705/2 |
| 6,463,417 B1 * | 10/2002 | Schoenberg | ............ | 705/2 |
| 7,349,859 B1 * | 3/2008 | Lamer et al. | ............ | 705/3 |
| 2001/0049610 A1 * | 12/2001 | Hazumi | ............ | 705/3 |
| 2001/0053986 A1 * | 12/2001 | Dick | ............ | 705/3 |
| 2002/0162005 A1 | 10/2002 | Ueda et al. | | |
| 2003/0154274 A1 | 8/2003 | Nakamura | | |
| 2006/0195341 A1 * | 8/2006 | Haaksma et al. | ............ | 705/3 |

* cited by examiner

*Primary Examiner*—Kambiz Zand
*Assistant Examiner*—Teshome Hailu
(74) *Attorney, Agent, or Firm*—Schiff Hardin LLP

(57) ABSTRACT

In a method and arrangement for control of the access to sensitive data stored in a first apparatus a first user of a first apparatus is notified of an access by the second apparatus to sensitive data stored in the first apparatus, and the notification is transmitted to the second apparatus. A first unique identification of the first user is requested by the first apparatus. A second unique identification of a second user of the second apparatus by the second apparatus. A check of the constellation (acquired via the requests) of the first and second users is made using a predetermined association file, the association file associating one or more allowed second users with each first user. Enablement of access of the second apparatus to the sensitive data stored in the first apparatus is prevented when the check of the association establishes an allowed constellation of first and second users. Access of the second apparatus to the sensitive data stored in the first apparatus is prevented when the check of the association establishes no allowed constellation of first and second users or access of the second apparatus to the sensitive data stored in the first apparatus has not been declared by the first user.

22 Claims, 3 Drawing Sheets

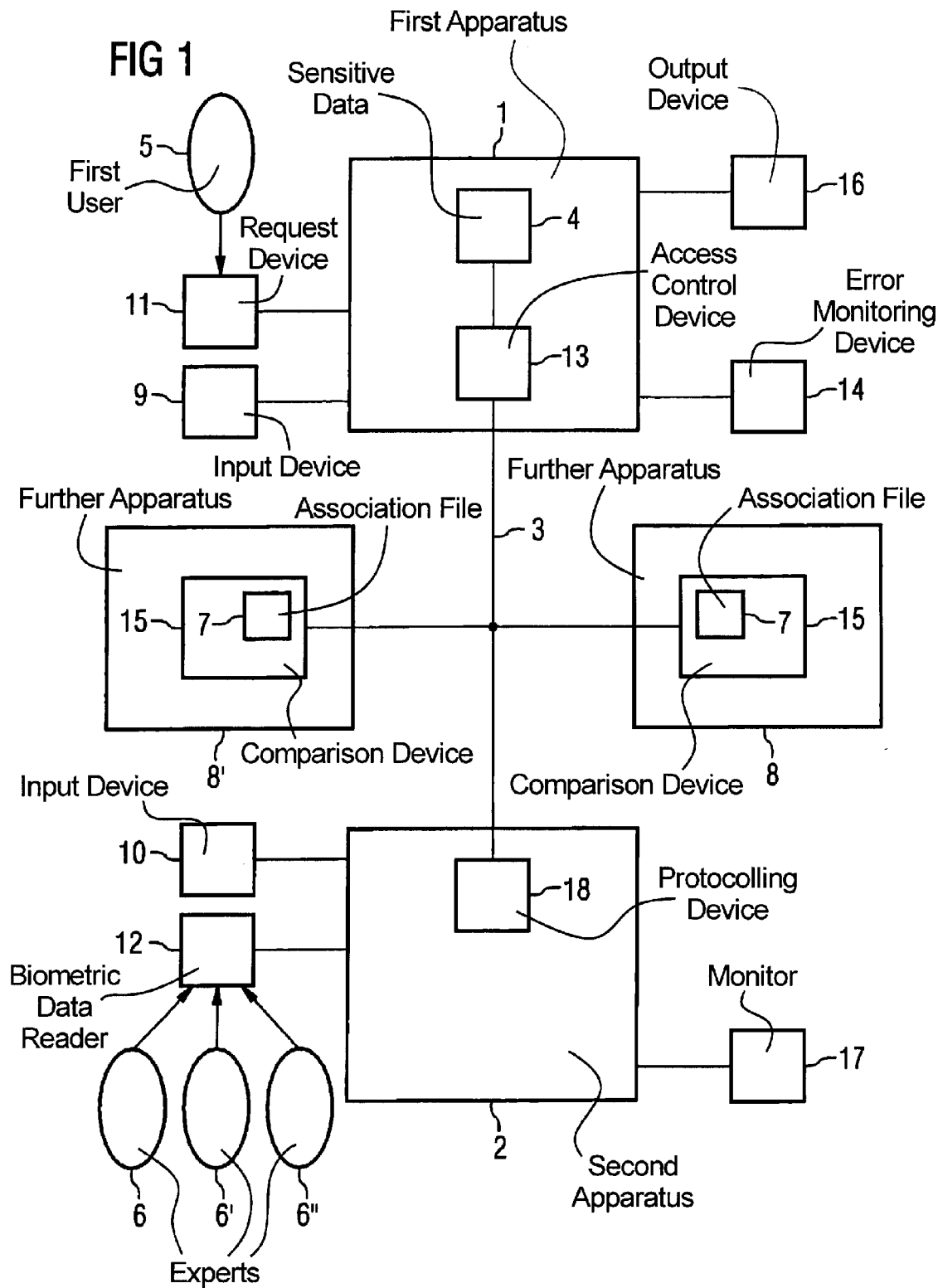

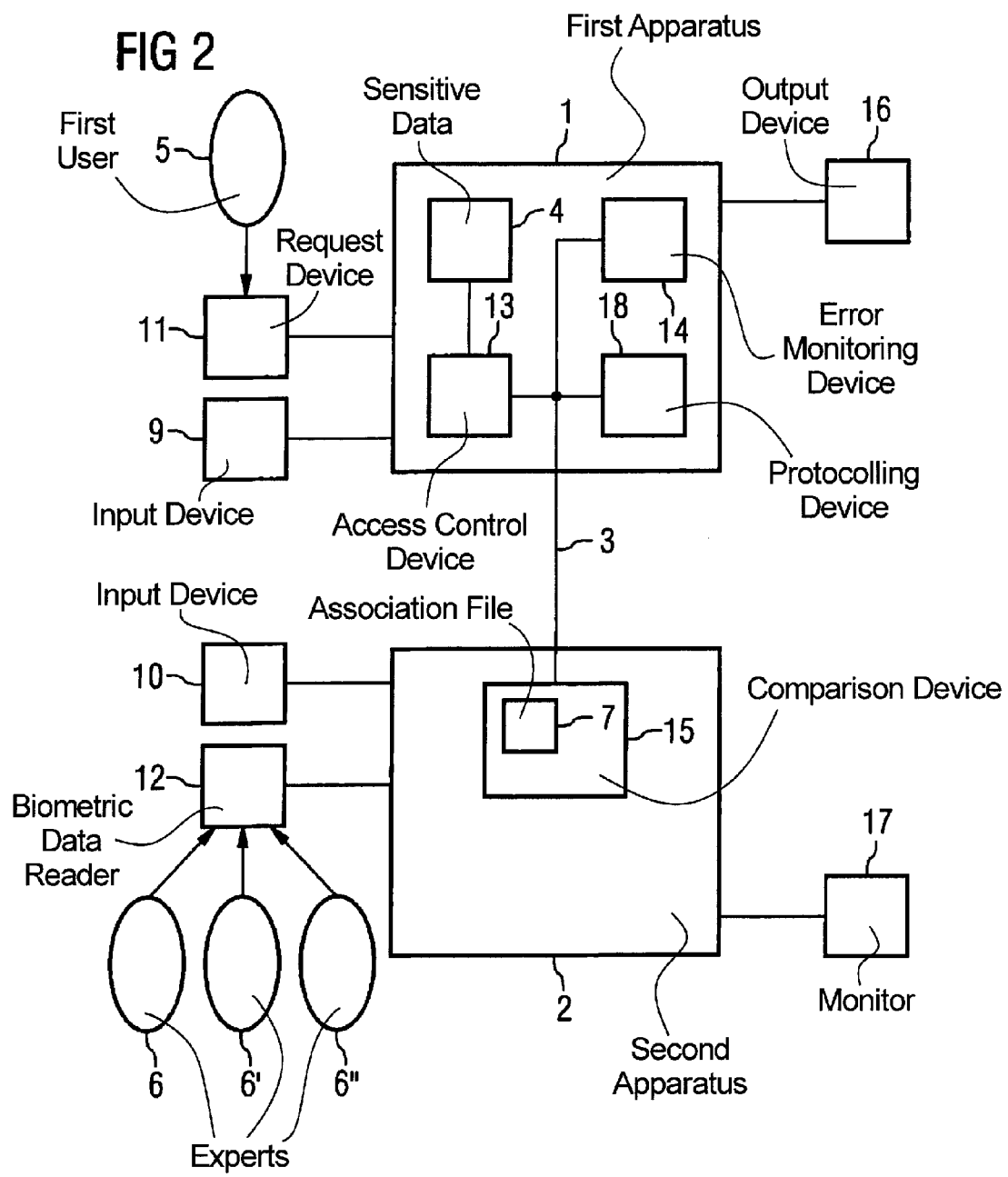

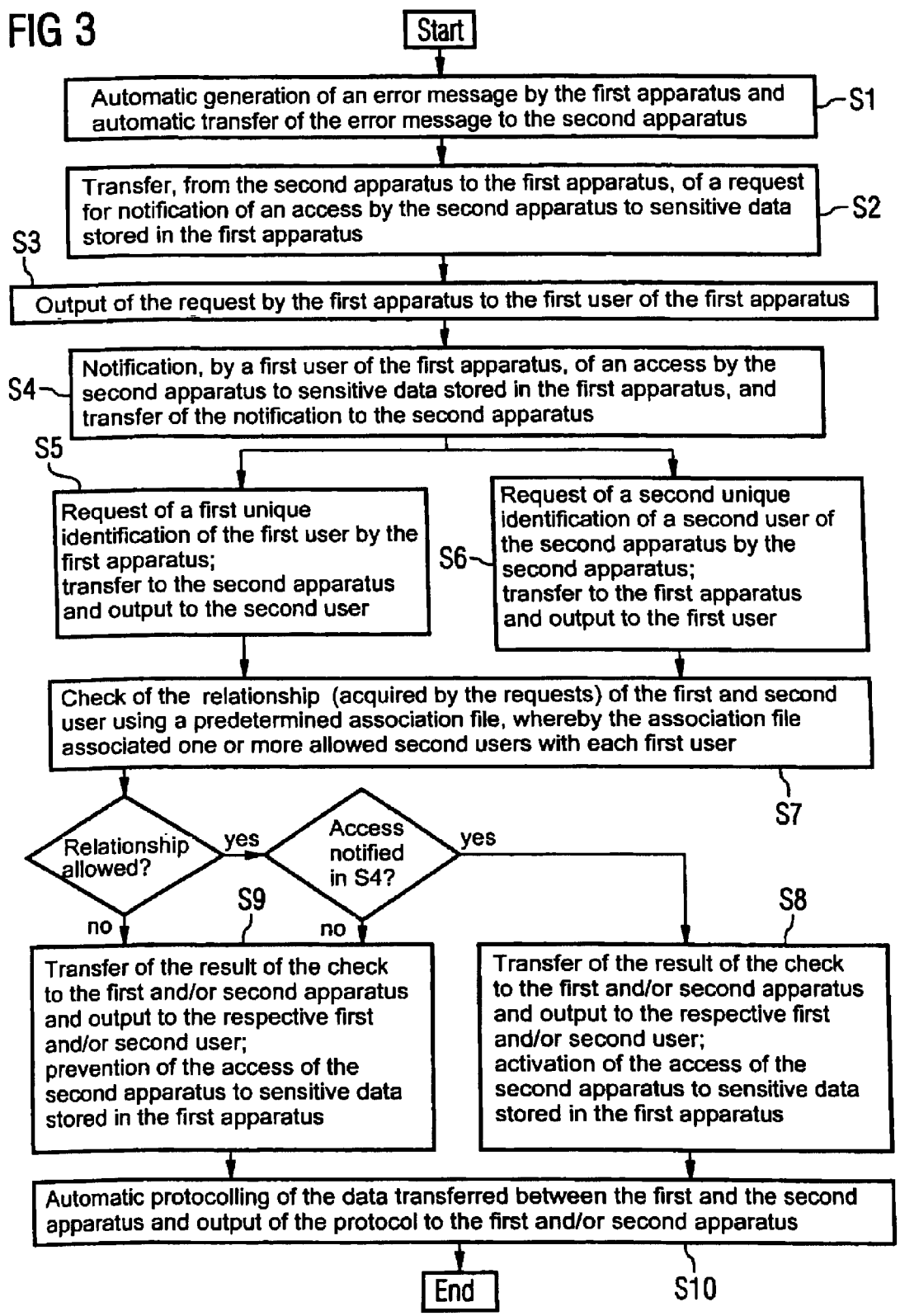

METHOD AND ARRANGEMENT FOR CONTROLLING ACCESS TO SENSITIVE DATA STORED IN AN APPARATUS, BY ANOTHER APPARATUS

BACKGROUND OF THE INVENTION

1. Field of the Invention

The present invention concerns a method and an arrangement for controlling access to stored, sensitive data, in particular for controlling access by one apparatus to sensitive data stored in another apparatus.

2. Description of the Prior Art

Modern technical apparatuses, and in particular medical apparatuses (for example magnetic resonance tomography systems) exhibit a high complexity. For example, given the malfunction of a magnetic resonance tomography system it is frequently not sufficient to use a single, generally qualified employee to remedy the error. Rather, in many cases it is necessary to draw on specialized expertise for the respective error from among a pool of highly-qualified experts.

This is particularly problematic in the case of geographically distributed locations of the technical apparatuses, since such highly-qualified experts are not comparably available at all locations.

Moreover, in the event of an error message in a geographically-distributed arrangement of advanced technical apparatuses, the highly-qualified workers must cover long routes in order to repair a faulty technical apparatus.

The long service times of the experts dispatched for the repair have as a consequence long downtimes of the respective technical apparatuses.

In this context, it should be noted that such technical apparatuses are frequently controlled by complex software programs. The high complexity of the software used leads to a major part of the failures of complex technical apparatuses (such as, for example, magnetic resonance tomography system). Such systems fail less frequently due to hardware errors than due to software errors.

To solve this problem, in the prior art it is known to implement error (failure) correction of a software-controlled, complex, technical apparatus via remote maintenance.

For this, the technical apparatus is connected, for example, over the Internet with a service center at which a number of highly-qualified employees are collected.

In the case of a failure, the technical apparatus automatically sends an error message to the service center.

The experts collected at the service center analyze the failure using the transmitted error message and try to correct the failure by transferring of correct software to the technical apparatus over the Internet.

U.S. Application Publication No. 2003/0154274 discloses a system that allows an efficient data exchange within a network given the use of portable data stations. The system has a first data station that stores specific data as well as a second data station that controls access rights to the data stored in the first data station. The second data station authorities further data stations for access to desired date. For this purpose, the first data station receives a query in the form of a data token and, under the condition that the data token is valid, outputs the corresponding data to the requester. To create such a data token, it is necessary that a user of the first data station expressly agree to the respective data exchange with a user of a requesting data station.

Due to the general legal frameworks in effect in many countries, however, it is presently not possible to also use a remote maintenance system for medical apparatuses, because medical apparatuses almost always contain sensitive patient data and thus are subject to data protection regulations regarding patient privacy.

For example, according to the legal requirements in Germany, such sensitive patient data may be made accessible only to the patient's doctor or an assistant of the doctor designated by the doctor.

In order to be considered as an assistant of the doctor in the sense of the legal regulations, an expert used for the error correction of the medical apparatus must be known to the doctor, and the total number of the experts for whom the doctor is responsible must be severely limited. Only in this case can involvement of the respective experts in the organization of the doctor be permitted, whereby access to sensitive patient data is allowed.

As defined by the regulations for data protection, however, such sensitive data occur not only in the field of medicine, but also in other fields.

SUMMARY OF THE INVENTION

It, Is therefore an object of the present invention to provide a method and an arrangement for controlling access to sensitive data stored in a technical apparatus, which ensure (in a particularly simple but nevertheless reliable manner) that only persons legitimized by a respective user of the technical apparatus can obtain access to the sensitive data.

The object is achieved according to the present invention, by a method for controlling access to sensitive data, stored in a first apparatus, by a second apparatus connected with the first apparatus including the steps of notification, by a first user of the first apparatus, of an access by the second apparatus to sensitive data stored in the first apparatus, and transfer of the notification to the second apparatus, requesting a first unique identification of the first user by the first apparatus, requesting of a second unique identification of a second user of the second apparatus by the second apparatus, checking the relationship (determined via the requests) of the first and second users using a predetermined association file, whereby the association file associates one or more allowed second users with each first user, activating access of the second apparatus to sensitive data stored in the first apparatus when the check of the association establishes an allowed relationships of the first and second users, and preventing access of the second apparatus to sensitive data stored in the first apparatus when the check of the association establishes no allowed constellation of first and second users, or if access by the second apparatus to sensitive data stored in the first apparatus has not been declared (authorized) by the first user.

Since, according to the inventive method, access to sensitive data stored in the first apparatus is possible only after notification by the first user, the first user retains absolute control over the sensitive data.

By means of the unique identification of both the (first) user of the first apparatus and of the (second) user of the second apparatus, before allowing access to sensitive data it is ensured that the (second) user of the second apparatus belongs to a predetermined group of people that are authorized by the respective (first) user of the first apparatus for access to the sensitive data.

By the inventive use of an association file, the group of (second) users legitimized for access to the sensitive data can be established in a particularly simple manner for a particular first user and be adapted to him or her. This is particularly of significance in order to enable remote maintenance in the case of a first technical apparatus that is used by a number of first users.

The access to a predetermined association file in which one or more allowed second users are associated for every first user additionally exhibits a high transparency and legal security that enables the first user to maintain, in a particularly simple manner via readout of the association file, a continuous overview of second users who are legitimized for access to sensitive data of the respective first user.

In summary, by means of the inventive method, remote maintenance by means of second technical apparatuses can be implemented a (first) technical apparatuses in which sensitive data are stored. The advantages associated with such remote maintenance, such as a significant time saving in the error correction and the availability of multiple experts, are thus now available for technical apparatuses containing sensitive data.

According to a preferred exemplary embodiment, the step of notification by the first user of an access by the second apparatus to sensitive data stored in the first apparatus requires the steps of transferring, by the second apparatus to the first apparatus, a request for notification of an access of the second apparatus to data stored in the first apparatus, and output of the request by the first apparatus to the first user of the first apparatus.

It is particularly advantageous for the step of the transferring the request by the second apparatus for notification of an access by the second apparatus to sensitive data stored in the first apparatus to ensue only after receipt of a communication generated by the first apparatus and transferred to the second apparatus.

Control over the initiation of the inventive method thus remains with the first apparatus.

In this case, it is particularly advantageous for the communication transferred from the first apparatus to the second apparatus to be an automatically generated and/or transferred error message.

It is thus ensured that a request for notification of an access of the second apparatus to sensitive data stored in the first apparatus is possible only in the event of an error with the first apparatus.

So that an access to sensitive data is not enabled in cases in which the transfer of sensitive data is not at all necessary for an error correction, it is also advantageous for the step of the transfer of a request by the second apparatus for notification of an access by the second apparatus to sensitive data stored in the first apparatus to ensue only after a check of the communication by the user of the second apparatus.

In order to increase the error tolerance of the inventive method against manipulation of the second apparatuses, it is particularly advantageous for the request of the unique identification of the second user of the second apparatus to ensue under monitoring by the first apparatus. This is possible without further difficulty by requiring the request of an individual password over a data network.

In order to provide knowledge about the respective user of the other apparatus to the first or second user of the first or second apparatus, the result of the request of the first unique identification of the first user of the first apparatus is transmitted to the second apparatus and is output to the second user and/or the result of the request of the second unique identification of the second user of the second apparatus is transferred to the first apparatus and is output to the first user.

By forwarding this information to the respective user, the transparency of the inventive method is increased, which improves the control by a respective user.

The request of a unique identification of a user preferably includes the request of an individual password and/or a biometric attribute and/or an electronic signature and/or an individual, machine readable article (for example a magnetic card or a coded transponder).

Such unique identification possibilities generally are entrusted to the user of technical apparatuses. Furthermore, the request of such unique identification attributes of users has proven to be reliable in practice.

Checking the constellation (acquired via the request) of the first and second user according to the inventive method alternatively can ensue via the first apparatus and/or via the second apparatus and/or via one or more further apparatuses connected with the first or second apparatus. The association file is stored in the respective apparatus or apparatuses.

It is also particularly advantageous for the result of the checking of the constellation (acquired via the request) of the first and second users using the association file to be transferred to the first and/or second apparatus and is output to the respective first and/or second user.

The first and/or second user thus obtains knowledge about whether access to the sensitive data is possible.

In order to further increase the transparency of the inventive method, and to ensure the monitoring and traceability of the release of sensitive data, it is particularly advantageous to include the further step in the automatically protocolling the data transferred between the first and the second apparatus and an output of the protocol to the first and/or second apparatus.

So that, in the event of an error, an uninterrupted correction of the error is also possible by a second person stored in the association file but not yet associated with the first person, the inventive method additionally includes the step of transferring an authorization form to the first apparatus by the second apparatus.

The first apparatus preferably is a medical system and the second apparatus preferably is a maintenance system for remote maintenance of the medical system.

In this case, the sensitive date are patient data stored in the medical system.

The above object also is inventively achieved by an arrangement for the control of the access to sensitive data stored in a first apparatus by a second apparatus connected with the first apparatus, which includes a data transfer device, connected with the first and second apparatus, for transfer of data between the first apparatus and the second apparatus, a first input device, connected with the first apparatus, for notification (by a first user of the first apparatus) of an access by the second apparatus to sensitive data stored in the first apparatus, a first request device, connected with the first apparatus, for the request of a first unique identification of the first user by the first apparatus, a second request device, connected with the second apparatus, for request of a second unique identification of a second user of the second apparatus by the second apparatus, and a comparison device, connected with the first and second apparatus, for checking the constellation (acquired by the first and second request device) of the first and second user using a predetermined association file, the association file associating one or more allowed second users with each first user and is stored in the comparison device.

The first apparatus has an access control device that is fashioned to approve the access of the second apparatus to sensitive data stored in the first apparatus when the comparison device establishes an allowed constellation of first and second user, and to prevent the access of the second apparatus to sensitive data stored in the first apparatus when the comparison device establishes no allowed constellation of first and second user, or no access by the second device to sensitive data stored in the first apparatus has been requested via the first input device.

In a preferred embodiment, the arrangement also has an error monitoring device, connected with the first apparatus, for automatic generation and transmission of error messages to the second apparatus via the data transfer device, a second output device, connected with the second apparatus, for output to the second user of the second apparatus of an error message received from the first apparatus, a second input device for transfer of a request of notification of an access by the second apparatus to sensitive data stored in the first apparatus after receipt of an error message transferred from the first apparatus to the second apparatus. And a first output device, connected with the first apparatus, for output of the request to the first user of the first apparatus.

The first request device preferably transfers the result of the request of the first unique identification of the first user of the first apparatus via the data transfer device to the second apparatus, and the second output device outputs the result of the request to the second user.

The second request device can transfer the result of the request of the second unique identification of the second user of the second apparatus via the data transfer device to the first apparatus, and the first output device can output the result of the request to the first user.

The first request device and the second request device can request an individual password and/or a biometric attribute and/or an electronic signature and/or an individual, machine-readable article.

The comparison device can be located in the first apparatus and/or in the second apparatus and/or in one or more further devices connected with the first or second apparatus.

The comparison device preferably transfers the comparison results via the data transfer device to the first and/or second apparatus, and the first output device outputs to the first user the comparison result acquired from the comparison device, and the second output device outputs to the second user the comparison result acquired from the comparison device.

The arrangement also preferably has a protocolling device in order to automatically create a protocol of the data transferred between the first and the second device, and to transfer the protocol via the data transfer device to the first and/or second apparatus.

Preferably the second apparatus transfers (via the data transfer device) an authorization form to the first apparatus.

Preferably the second apparatus is a maintenance system for remote maintenance of the first apparatus.

The first apparatus is thereby preferably a medical system, and the second apparatus is a maintenance system for remote maintenance of the medical system.

In this case, the sensitive data are patient data stored in the medical system.

DESCRIPTION OF THE DRAWINGS

FIG. 1 is a block diagram of a preferred exemplary embodiment of the inventive arrangement.

FIG. 2 is a block diagram of an alternative exemplary embodiment of the inventive arrangement.

FIG. 3 is a flow chart of the inventive method.

DESCRIPTION OF THE PREFERRED EMBODIMENTS

FIG. 1 is a block diagram of a preferred exemplary embodiment of the inventive arrangement for control of the access to sensitive data stored in a first apparatus.

The arrangement has a first apparatus 1, which, according to this embodiment, is a medical system. The medical system 1 can be, for example, a magnetic resonance tomography apparatus or a computed tomography apparatus.

The medical system 1 contains sensitive data 4 that are stored in a suitable data medium, for example a disk. According to the embodiment described herein, these sensitive data are patient data, for example, CT or MR images of patients.

The medical system also has an access control device 13 that is fashioned in order to allow or prevent the access to the sensitive data 4 stored in the medical system. In the preferred exemplary embodiment, the access control device 13 is a microprocessor that can access the sensitive data 4 stored on the data medium of the medical system 1.

A first input device 9 (in the present embodiment a keyboard) for notification of an access to sensitive data stored in the first apparatus by a first user 5 of the medical system 1 is connected with the medical system 1. According to the present embodiment, the first user 5 of the medical system is a doctor.

A first request device 11 in the form of a magnetic card reader is connected to the medical system 1. The magnetic card reader 11 is fashioned to enable a first unique identification of the doctor 5 via readout of an individual magnetic card of the doctor 5.

Also connected with the medical system 1 are an error-monitoring device 14 for monitoring of the function of the medical system 1 and a first output device 16 for output to the doctor 5 of information received or generated by the medical system 1.

In the present embodiment, the error-monitoring device 14 is a microprocessor and the first output device 16 is a monitor.

The medical system 1 is connected via a data transfer device 3 with a second apparatus 2, which is a maintenance system for maintenance of the medical system 1. The data transfer device 3 enables a transfer of data between the medical system 1 and the maintenance apparatus 2.

In the exemplary embodiment, the data transfer device 3 is a secured Internet connection via which suitable encoded data are transferred between the medical system 1 and the maintenance system 2.

The maintenance system 2 is fashioned for remote maintenance of the medical system 1 over the secured Internet connection 3.

For this, maintenance system 2 comprises, among other things, a second request device 12 that, in the present exemplary embodiment, is a reader for the biometric data of an expert 6, 6', 6" attending the maintenance system 2.

The reader for biometric data can be fashioned, for example, for readout of the iris or the fingerprint of the expert 6, 6', 6". The reader for biometric data 12 thus enables a unique identification of an expert 6, 6', 6" (second user) using the maintenance system 2.

Also connected with the maintenance system 2 are a second input device 10, for example a mouse, as well as a second output device 17 which can in turn be monitor.

The mouse enables the expert 6, 6', 6" to control the maintenance system 2.

Data generated by the maintenance system 2 or received from the medical system 1 via the Internet connection 3 can be output to the experts 6, 6', 6" via the monitor 17.

According to the preferred exemplary embodiment, a protocolling device 18 in the form of a microprocessor connected with a disk is arranged in the maintenance system 2.

The protocolling device 18 is suitable for automatically creating a protocol of the data transferred between the medical system 1 and the maintenance system 2, for storing the protocol on the disk, and for transferring the protocol to the medical system 1 via the secured Internet connection 3. The protocol generated by the protocolling device 18 can be output to the doctor 5 or the experts 6, 6', 6" by the medical system 1 via the monitor 16 and by the maintenance system 2 via the monitor 17. The protocol can contain, for example, contain the names of the people participating in the data exchange, the time, the type of the data access (copy, deletion, insertion) as well as a specification of the respective data.

The inventive arrangement for control of the access to sensitive data 4 stored in the medical system 1 also has a comparison device 15 connected over the secured Internet connection 3 with the medical system 1 and the maintenance system 2.

Stored in the comparison device 15 is an association file 7 in which one or more allowed experts 6, 6', 6" for the maintenance system 2 are associated in tabular form with each doctor 5 using the medical system 1.

Using the association file 7, it is thus possible for the comparison device 15 to check a constellation (acquired by the magnetic card reader 11 and the reader for biometric data 12) of doctor 5 and experts 6, 6', 6" with regard to its validity. For this, the comparison device 15 is preferably a suitable microprocessor. The association file 7 can be stored in a fixed storage system or a suitable data medium.

In the exemplary embodiment shown in FIG. 1, two comparison devices 15 are provided that are arranged in two further apparatuses 8, 8'. These further apparatuses 8, 8' are servers monitoring the data transfers that are connected with the medical system 1 and the maintenance system 2 over the secured Internet connection. Naturally, the further apparatuses 8, 8' can also be other systems.

By virtue of design of the comparison device 15, manipulations can be safely prevented and a high data security thus can be ensured.

The comparison devices 15 of the further apparatuses 8, 8' are fashioned in order to allow the access by the maintenance system 2 to patient data 4 stored in the medical system 1 via corresponding control of the access control device 13 when (using the association file 7) an allowed constellation of doctor 5 and experts 6, 6', 6" has been established. The comparison devices 15 of the further apparatuses 8, 8' are also fashioned in order to prevent the access by the maintenance system 2 to patient data 4 stored in the medical system 1 via corresponding control of the access control device 13 when the comparison device 12 has established no allowed constellation of doctor 5 and experts 6, 6', 6", or no access by the maintenance system 2 to patient data 4 stored in the medical system 1 has been sought via the keyboard 9.

Since at least one notification via the medical system 1 is necessary for a release of the patient data, a doctor 5 operating the medical system 1 always retains complete control over the patient data 4 stored in the medical system 1.

Via the comparison devices 15 it is thus ensured that only experts 6, 6', 6" known to the doctor 5 and authorized by the doctor 5, who are assigned to the operation of the doctor, can obtain knowledge of patient data 4 stored in the medical system 1.

Remote maintenance of the medical system 1 by the maintenance system 2 is thus possible with the inventive arrangement.

According to the exemplary preferred embodiment of FIG. 1, access to sensitive patient data 4 stored in the medical system 1 is initialized by the error monitoring device 14 that, given determination of an error in the medical system 1, automatically generates an error message and transmits it to the maintenance system 2 via the secured Internet connection 3.

The error message is output to experts 6, 6', 6" operating the maintenance system 2 via the monitor 17 of the maintenance system 2.

Alternatively, the error message can be manually transmitted to the maintenance system 2 by the doctor 5 over, for example, a normal telephone line in the framework of a telephone conversation.

Using the error message, the expert/experts 6, 6', 6" decide/decides whether an access to the sensitive patient data 4 stored in the medical system 1 is absolutely necessary for correction of the error in the medical system 1.

If, due to the error message generated by the error monitoring device 14 of the medical system 1 and transmitted to the maintenance system 2, the experts 6, 6', 6" are convinced that access to sensitive patient data 4 is necessary to correct the error in the medical system 1, via the maintenance system 2 and the data transfer device 3 the expert/experts causes/cause transmission to the medical system 1 of a request for notification of an access by the maintenance system 2 to the patient data 4 stored in the medical system 1.

The request for notification of access of the maintenance system 2 to the sensitive patient data 4 stored in the medical system 1 is displayed to the doctor 5 via the monitor 16 of the medical system 1.

The doctor 5 (or a person legitimized by the doctor 5 for this task, who is included in the organization of the doctor 5 in a suitable manner) thus again has an opportunity to approve the initiation of a data exchange.

In order to notify both the doctor 5 operating the medical system 1 and the experts 6, 6', 6" operating the maintenance system 2 about the respective operator of the other system, both the magnetic card reader 11 and the reader for biometric data 12 are fashioned in order to transfer (via the secured Internet connection 3) the result of the request of the first and second unique identification of the doctor 5 or, respectively, the experts 6, 6', 6" to the respective other system, where it is displayed via the respective monitor 16, 17.

A manual check of the respective user of the respective system by the respective other user of the other system is possible.

In order to notify the doctor 5 and the experts 6, 6', 6" of the respective function state of the inventive arrangement, the comparison devices 15 are also fashioned to transfer (via the secured Internet connection) the result of the comparison to the medical system 1 and the maintenance system 2, where they are output to the doctor 5 or the experts 6, 6', 6" by the monitor 16 or the monitor 17.

Should the constellation (established by the comparison device 15) of the doctor 5 and the experts 6 not presently allow an access to sensitive patient data 4 stored in the medical system 1, the maintenance system 2 according to the embodiment shown in FIG. 1 is also fashioned to transfer (via the secured Internet connection 3) to the medical system 1 an authorization form in the form of a fax form.

The fax form can be printed out by the medical system 1 via a printer (not shown in FIG. 1).

The authorization form (fax form) is to be filled out by the doctor 5 and be sent, signed, to the further apparatuses 8, 8', where the new constellation of doctor 5 and experts 6, 6', 6" is entered into the respective association file 7.

The inventive arrangement thus allows a flexible adaptation to the current situation in a simple and still secure manner, such that a remote maintenance of a medical system 1 via the maintenance system 2 can be quickly ensured in every case.

If necessary, transfer of the patient information 4 by the experts 6, 6', 6" to a further person can also be legitimized by the doctor 5 (or a person legitimized by the doctor) via the authorization form.

FIG. 2 shows an alternative exemplary embodiment of the inventive arrangement for controlling access, by a second apparatus 2 connected with the first apparatus 1 via a data transfer device 3, to sensitive data 4 stored in a first apparatus 1, in which elements identical to those in FIG. 1 are provided with the same reference characters.

The alternative exemplary embodiment shown in FIG. 2 differs from the preferred exemplary embodiment shown in FIG. 1 in that the comparison device 15, and therewith the association file 7 is not arranged in a further apparatus 8, 8', but rather is integrated into the maintenance system 2. A redundancy of the comparison device 14 thus is not provided in the exemplary embodiment shown in FIG. 2.

The exemplary embodiment shown in FIG. 2 also differs from the exemplary embodiment shown in FIG. 1 in that the protocolling device 18 is not arranged in the maintenance system 2, but rather is arranged in the medical system 1, and the error monitoring device 14 is integrated in the medical system 1.

Although in FIGS. 1 and 2 described in the preceding, the comparison device 15 is arranged either in separate further apparatuses 8, 8' or in the maintenance system 2, it is naturally also possible to provide the comparison device 15 in the medical system 1 or both in the medical system 1 and in the maintenance system 2.

Furthermore, instead of the magnetic card reader 11 and the reader for biometric data 12, it is alternatively possible to provide any type of request device that is fashioned to request an individual password and/or a biometric attribute and/or an electronic signal and/or an individual machine-readable article.

An individual machine-readable article can be, for example, a magnetic card or an article provided with an individual bar code or individually encoded transponder that is suitable for unambiguously identifying a person.

Those skilled in the art will appreciate that the inventive arrangement is not only suitable for remote maintenance of medical systems, but also can be used, for example, in the framework of any remote diagnostic. In this case, the second apparatus 2*n* is a remote diagnostic apparatus that allows an access to the medical system 1, and the second users 6, 6', 6" operating the remote diagnostic apparatus 2 are a [sic] doctor, operating the remote diagnostic apparatus 2, who accesses the patient data 4 acquired by the first doctor 5 operating the medical system 1.

Although only monitors 16 and 17 are shown in FIGS. 1 and 2 for the output of data, naturally any other output devices for data can be used, for example printers, etc. Data input is not only possible via a keyboard 9 or a mouse 10 as in FIGS. 1 and 2, but also by means of any other input media such as, for example, touch screens or trackballs.

Furthermore, the data transfer device 3 does not have to be a secure Internet connection, but rather any other type of connection (such as, for example, a direct connection over, for example, a telephone line or a secured line or a transfer over an air interface) can be used.

In the exemplary embodiment shown in FIGS. 1 and 2, the request of each of the first and the second unique identifications of the first and second users 5, 6, 6', 6" simultaneously ensues respectively via the medical system 1 or the maintenance system 2 under the control of the medical system 1. Alternatively, the request can ensue sequentially via control of the maintenance system 2, or separately via the respective system.

The inventive method for controlling access to sensitive data stored in a first apparatus is explained in detail with reference to FIG. 3.

As shown in FIG. 3, in a first step S1 an error message is automatically generated by the first apparatus 1 and automatically transmitted to the second apparatus 2. The transfer of the error message can ensue via telephone or a data line.

In the subsequent step S2, as a result of the received error message a request for notification of an access by the second apparatus 2 to sensitive data 4 stored in the first apparatus 1 is transmitted to the first apparatus 1 by the second apparatus 2 via a suitable data transfer device 3. The transmission of the request for notification of an access only ensues in this exemplary embodiment after a check of the error message by a user 6 of the second apparatus 2.

In step S3, the request for notification of an access is output by the first apparatus 1 to a first user 5 of the first apparatus 1.

After output of the request to the first user 5, (at the choice of the first user 5) in step S4 the notification of the access by the second apparatus 2 to sensitive date 4 stored in the first apparatus 1 ensues via the first user 5 of the first apparatus 1. This notification is transferred to the second apparatus 2 via the data transfer device 3.

Subsequently, in step S5 a first unique identification of the first user 5 is requested by the first apparatus 1 and is transmitted via the data transfer device 3 to the second apparatus 2 for output to the second users 6, 6', 6".

At the same time, in a parallel step S6 a second unique identification of the second user 6, 6', 6" of the second apparatus 2 is requested by the second apparatus 2 and is transmitted to the first apparatus 1 for output to the second users 5.

It is obvious that the steps S5 and S6 can alternatively also be sequentially implemented, whereby optionally the step S6 ensues on [sic] the step S5 or the step S5 ensues on the step S6.

In the step S7 subsequent to the steps S5 and S6, the constellation (acquired by the requests) of the first and second users 5, 6, 6', 6" is checked using a predetermined association file 7, whereby the association file 7 associates one or more allowed second users 6, 6', 6" with each first user 5.

It is subsequently decided whether the constellation acquired by the requests is allowed.

If this is not the case, in step S9 the result of the check is transferred to the first and/or second apparatus 1, 2 and is output to the respective first and/or second users 5, 6, 6', 6". The access by the second apparatus 2 to sensitive data 4 stored in the first apparatus 1 is also prevented.

If the check results in affirmation that the constellation is allowed, it is subsequently checked in step S4 whether access by the second apparatus 2 to sensitive data 4 stored in the first apparatus 1 has been sought.

If this is the case, in the subsequent step S8 the result of the checks is transferred to the first and/or second apparatus 1, 2 and there is output to the respective first and/or second users 5, 6, 6', 6". Access by the second apparatus 2 to the sensitive data 4 stored in the first apparatus 1 is also approved.

If in step S4 no access has been sought, the method proceeds with the step S9 specified in the preceding.

In the step S10 following the steps S8 and S9, the data transferred between the first and second apparatus 1, 2 are automatically protocolled, and the protocol thus created is output to the first and second apparatuses 1 and 2.

The inventive method ends with this step.

Those skilled in the art will appreciate that the check as to whether access has been sought for in step S4 can ensue (differently from that shown in FIG. 3) immediately after the step S4 and thus before the steps S5 and S6. In this case, the steps S5 and S6 are proceeded with when an access has been sought in step S4. Otherwise, the method proceeds with step S9.

The request of a unique identification of a user 5, 6 preferably includes the request of an individual password and/or a biometric attribute and/or an electronic signal and/or an individual, machine-readable article.

The check of the constellation (acquired via the request) of the first and second users 5, 6 preferably ensues via the first apparatus 1 and/or via the second apparatus 2 and/or via one or more further apparatuses 8, 8' connected with the first and second apparatus 1, 2, whereby the association file 7 is stored in the respective apparatus or apparatuses 1, 2, 8, 8'.

If the check of the constellation of the first and second users 5, 6, 6', 6" results in the determination that such a constellation is not stored as being allowed in the association file 7, according to a further exemplary embodiment not shown in FIG. 3, the inventive method also includes the step of communicating an authorization form from the second apparatus 2 to the first apparatus 1. Such an authorization form also can be sent when a forwarding of the sensitive data 4 by the second user 6, 6', 6" to a third party is necessary.

It is particularly advantageous for the second apparatus 2 to be is a maintenance system for remote maintenance of the first apparatus 1.

It is also particularly advantageous for the first apparatus 1 to be a medical system and the second apparatus 2 to be a maintenance system for the remote maintenance of the medical system. In this case, the sensitive data 4 are patient data stored in the medical system.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for controlling access to sensitive data stored in a first apparatus by a second apparatus in communication with the first apparatus, comprising the steps of:

upon a request by the second apparatus, operated by a second user, to access sensitive data stored in the first apparatus, generating a notification at said first apparatus of said request to access, and prompting a first user of the first apparatus to transmit said notification to the second apparatus;

said first apparatus also requesting a first unique identification of said first user;

at said second apparatus upon receipt of said notification, requesting a second unique identification of the second user of the second apparatus by the second apparatus;

accessing from said first apparatus an association file wherein at least one second user is stored in a stored association with each first user, and checking whether the second user identified by said second unique identification has a predetermined association in said association file with said first user identified by said first unique identification; accessing by said second apparatus to the sensitive data stored in the first apparatus if said predetermined association is found in said association file; and preventing access by said second apparatus to the sensitive data stored in the first apparatus if no predetermined association is found in said association file between the second user identified by said second unique identification and the first user identified by said first unique identification, or if access by said second apparatus to the sensitive data stored in the first apparatus has not been declared by said first user.

2. A method as claimed in claim 1 comprising transferring a request by said second apparatus for said notification only after receiving, at said second apparatus, a communication generated by the first apparatus and transmitted to the second apparatus.

3. A method as claimed in claim 2 comprising automatically generating said communication at said first apparatus and automatically transmitting said communication from said first apparatus to said second apparatus.

4. A method as claimed in claim 2 comprising transferring said request for notification by said second apparatus only after checking said communication at said second apparatus by said second user.

5. A method as claimed in claim 1 comprising controlling at said first apparatus said request for said second unique identification of said second user of said second apparatus.

6. A method as claimed in claim 1 comprising generating a result of said request for said first unique identification of said first user of said first apparatus, and transmitting said result to said second apparatus and outputting said result at said second apparatus to said second user.

7. A method as claimed in claim 1 comprising generating a result of said request for said second unique identification of said second user of said second apparatus, and transmitting said result from said second apparatus to said first apparatus and outputting said result at said first apparatus to said first user.

8. A method as claimed in claim 1 comprising including, in each of said request for said first unique identification of said first user and said request for said second unique identification of said second user, a request for an identifier selected from the group consisting of a password, a biometric feature, an electronic signature and an individualized machine-readable article.

9. A method as claimed in claim 1 comprising conducting said check of said association file at a location selected from the group consisting of said first apparatus, said second apparatus and a further apparatus connected to one of said first apparatus or said second apparatus.

10. A method as claimed in claim 1 comprising outputting a result of checking said association file at a location selected from said first apparatus and said second apparatus.

11. A method as claimed in claim 1 comprising automatically protocolling all data transferred between said first apparatus and said second apparatus and outputting said protocol to said first apparatus and said second apparatus.

12. A method as claimed in claim 1 comprising, if access to said sensitive data stored at said first apparatus is not enabled, transferring an authorization form to the first apparatus from the second apparatus.

13. A method as claimed in claim 1 comprising employing, as said second apparatus, a maintenance system for remote maintenance of said first apparatus.

14. A method as claimed in claim 1 comprising employing, as said first apparatus, a medical system and employing as said second apparatus, a maintenance system for remote maintenance of said medical system.

15. A method as claimed in claim 14 comprising storing patient data in said medical system as said sensitive data.

16. An arrangement for controlling access to sensitive data stored in a first apparatus by a second apparatus in communication with the first apparatus, comprising:
- a first apparatus operated by a first user and a second apparatus, operated by a second user, configured to communicate with each other;
- upon receipt at the first apparatus of a request from the second apparatus for access by the second apparatus to the sensitive data stored in the first apparatus, said first apparatus being configured to generate a notification of said request for access to said first user, and to generate a prompt for said first user to transmit said notification to the second apparatus;
- said first apparatus also being configured to request a first unique identification of the first user of said first apparatus;
- said second apparatus being configured, upon receipt of said notification, to request a second unique identification of the second user of the second apparatus;
- a memory having an association file stored therein wherein at least one second user is stored in a stored association with each first user;
- said first apparatus being configured to access said memory and to check whether the second user identified by said second unique identification has a predetermined association in said association file with said first user identified by said first unique identification;
- said first apparatus being configured to enable access by said second apparatus to the sensitive data stored in the first apparatus if said predetermined association is found in said association file; and
- said first apparatus being configured to prevent access by said second apparatus to the sensitive data stored in the first apparatus if no predetermined association is found in said association file between the second user identified by said second unique identification and the first user identified by said first unique identification, or if access by said second apparatus to the sensitive data stored in the first apparatus has not been declared by said first user.

17. An arrangement as claimed in claim 16 wherein said second apparatus is configured to transmit said request for access only after receiving, at said second apparatus, a communication generated by the first apparatus and transmitted to the second apparatus.

18. An arrangement as claimed in claim 16 comprising a protocolling unit for automatically protocolling all data transferred between said first apparatus and said second apparatus and outputting said protocol to said first apparatus and said second apparatus.

19. An arrangement as claimed in claim 16 wherein said second apparatus, if access to said sensitive data stored at said first apparatus is not enabled, is configured to transmit an authorization form to the first apparatus from the second apparatus.

20. An arrangement as claimed in claim 16 wherein said second apparatus is a maintenance system for remote maintenance of said first apparatus.

21. An arrangement as claimed in claim 16 wherein said first apparatus is a medical system and said second apparatus is a maintenance system for remote maintenance of said medical system.

22. An arrangement as claimed in claim 21 wherein said memory contains patient data for said medical system as said sensitive data.

* * * * *